(12) United States Patent
Gericke et al.

(10) Patent No.: US 6,673,968 B1
(45) Date of Patent: Jan. 6, 2004

(54) METHOD OF PRODUCING N-(4,5-BIS-METHANESULFONYL-2-METHYL-BENZOYL)-GUANIDINE, THE HYDROCHLORIDE THEREOF

(75) Inventors: Rolf Gericke, Seeheim-Jugenheim (DE); Manfred Baumgarth, Darmstadt (DE); Hans Markus Bender, Ostermuenchen (DE); Bernhard Ladstetter, Ostermuenchen (DE)

(73) Assignee: Merck Patent Gesellschaft mit beschränkter Haftung, Darmstadt (DE)

( * ) Notice: Subject to any disclaimer, the term of this patent is extended or adjusted under 35 U.S.C. 154(b) by 0 days.

(21) Appl. No.: 10/111,542

(22) PCT Filed: Oct. 11, 2000

(86) PCT No.: PCT/EP00/09977

§ 371 (c)(1),
(2), (4) Date: Sep. 4, 2002

(87) PCT Pub. No.: WO01/30750

PCT Pub. Date: May 3, 2001

(30) Foreign Application Priority Data

Oct. 26, 1999 (DE) .......................................... 199 51 418

(51) Int. Cl.[7] ...................... C07C 277/08; C07C 279/02

(52) U.S. Cl. ...................................................... 564/237
(58) Field of Search ........................................... 564/237

(56) References Cited

U.S. PATENT DOCUMENTS 5,696,167 A * 12/1997 Gericke et al. .............. 514/618
5,744,641 A * 4/1998 Gericke et al. .............. 564/228

FOREIGN PATENT DOCUMENTS

EP      758 644      2/1997

OTHER PUBLICATIONS

Ulman et al: Journal of Organic Chemistry vol. 54, No. 19 pp. 4691–4692(1989).
Baumgarth et al: Journal of Medicinal Chemistry vol 40, No. 13 pp. 2017–2034 (1997).

* cited by examiner

Primary Examiner—Brian Davis
(74) Attorney, Agent, or Firm—Millen, White, Zelano & Branigan, P.C.

(57) ABSTRACT

The present invention relates to an NHE-1 selective Na+/H+ antiporter inhibitor N-(4,5-bismethanesulfonyl-2-methylbenzoyl)guanidine, hydrochloride, to its hydrochloride hydrate, and to a process for the preparation.

5 Claims, No Drawings

METHOD OF PRODUCING N-(4,5-BIS-METHANESULFONYL-2-METHYL-BENZOYL)-GUANIDINE, THE HYDROCHLORIDE THEREOF

The present invention relates to N-(4,5-bismethanesulfonyl-2-methyl-benzoyl)guanidine, hydrochloride hydrate, and to a process for the preparation of N-(4,5-bismethanesulfonyl-2-methylbenzoyl)guanidine, hydrochloride and the hydrochloride hydrate. N-(4,5-Bismethanesulfonyl-2-methylbenzoyl)guanidine, hydrochloride hydrate is an NHE-1 selective $Na^+/H^+$ antiporter inhibitor.

Sulfonylbenzoylguanidines are known and are described, for example, in EP 0 758 644 A1. These substances are inhibitors of the cellular $Na^+/H^+$ antiporter, i.e. they are active ingredients which inhibit the $Na^+/H^+$ exchange mechanism of the cells (Düsing et al., Med. Klin. 1992, 87, 367–384,) and are consequently good antiarrhythmic agents which are suitable, in particular, for the treatment of arrhythmia occurring as a consequence of oxygen deficiency.

The substances exhibit a good cardioprotective action and are therefore particularly suitable for the treatment of acute myocardial infarction, infarction prophylaxis, post-infarction treatment, chronic cardiac insufficiency and for the treatment of angina pectoris. They furthermore counter all pathological hypoxic and ischaemic damage, enabling the illnesses caused primarily or secondarily thereby to be treated. These active ingredients are likewise highly suitable for preventive applications.

Owing to the protective action of these substances in pathological hypoxic or ischaemic situations, further possible applications arise therefrom in surgical interventions for protection of organs with temporarily reduced supply, in organ transplants for protection of the removed organs, in angioplastic vascular or cardiac interventions, in ischemia of the nervous system, in the therapy of shock states and for the prevention of essential hypertonia.

These compounds can furthermore also be employed as therapeutic agents in illnesses caused by cell proliferation, such as arteriosclerosis, diabetes and late complications of diabetes, tumour illnesses, fibrotic illnesses, in particular of the lungs, liver and kidneys, and organ hypertrophia and hyperplasia. In addition, the compounds are suitable for diagnostic use for the recognition of illnesses accompanied by increased activity of the $NA^+/H^+$ antiporter, for example in erythrocytes, thrombocytes or leukocytes.

The compounds can therefore be used as medicament active ingredients in human and veterinary medicine. They can furthermore be used as intermediates for the preparation of further medicament active ingredients.

The invention had the object of finding a highly active compound having a very good oral absorption property.

N-(4,5-Bismethanesulfonyl-2-methylbenzoyl)guanidine, hydrochloride hydrate has proven to be a highly suitable and highly active substance and is distinguished by a particularly good oral absorption property. N-(4, 5-Bismethanesulfonyl-2-methylbenzoyl)guanidine, hydrochloride hydrate is therefore preferably administered in oral form.

The absorption from the digestive tract after oral administration can be calculated by comparison of the concentrations of the administered active ingredient determined in the blood plasma after oral and intravenous administration (dose-standardised $AUC_{po}/AUC_{iv}$) [AUC=area under the curve]. The rat exhibited an absorption rate of 98% (of the orally administered radioactively labelled substance). Bioavailabilities of the hydrochloride hydrate of from 88% to 99% were found in dogs, and 75% and 96% in 2 monkeys. Since the absorption rate is at least equal to or greater than the bioavailability determined, very good absorption has thus also been found in these animal species.

The invention therefore relates to N-(4,5-bismethanesulfonyl-2-methylbenzoyl)guanidine, hydrochloride hydrate. This invention is to be regarded as a selection invention to EP 0 758 644.

Since this substance is very promising, its preparation is of very considerable interest. The preparation of the free N-(4,5-bismethanesulfonyl-2-methylbenzoyl)guanidine base and its analogues has been described in EP 0 758 644 A1 cited above.

However, the known syntheses comprise a large number of individual steps, some of which have unsatisfactory yields and which also have environmentally polluting and hazardous reaction conditions, such as, for example, the reaction with methyl mercaptam or the oxidation of the thioether to give the sulfone.

There is therefore great interest in finding an improved process for the preparation of N-(4,5-bismethanesulfonyl-2-methylbenzoyl)guanidine, its hydrochloride and hydrochloride hydrate.

It was therefore likewise an object of the present invention to find a novel synthesis variant for the $Na^+/H^+$ antiporter which is shorter and also more effective compared with conventional methods.

The invention relates to a process for the preparation of the benzoylguanidine derivative N-(4,5-bismethanesulfonyl-2-methylbenzoyl)-guanidine, hydrochloride of the formula I

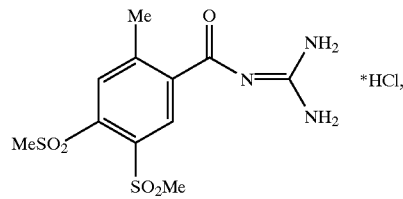

in which Me is methyl, and of the hydrochloride hydrate, which is characterised in that firstly, by reaction of the starting compound of the formula II

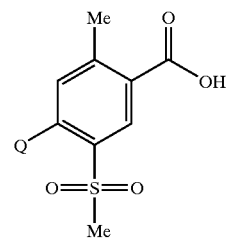

in which

Me is a methyl group, and Q is fluorine or chlorine, with a methanesulfinate in a nucleophilic substitution on the activated aromatic ring, the 4-methanesulfonyl group is introduced in a one-step reaction, then, in the second step, the compound of the formula III

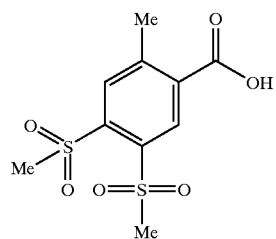

III is converted into an acid chloride and reacted with guanidine to give N-(4,5-bismethanesulfonyl-2-methylbenzoyl) guanidine,
and, in the third step, converted into the hydrochloride of the formula I and/or its hydrochloride hydrate by reaction in aqueous HCl.

The starting compound of the formula II is prepared, for example, starting from 2-bromo-5chlorotoluene by halogen-metal exchange and $CO_2$ treatment to give 4-chloro-2-methylbenzoic acid followed by reaction of 4-chloro-2-methylbenzoic acid with chlorosulfonic acid, sodium sulfite and methyl iodide to give 4-chloro-2-methyl-5-methylsulfonylbenzoic acid or by reaction of 2-bromo-5-chlorotoluene with methanesulfonic acid and thionyl chloride in a Friedel-Crafts-like reaction in the presence of a Friedel-Crafts catalyst to give 4-chloro-2-methyl-4-methylsulfonylphenyl bromide followed by exchange of the bromine by a carboxyl group through a palladium-catalysed carbonylation reaction in an autoclave under superatmospheric pressure and at elevated temperature to give 4-chloro-2-methyl-5-methyl-sulfonylbenzoic acid. The reaction conditions selected are known from the literature (lit.: Houben-Weyl, Methoden der Organ. Chemie [Methods of Organic Chemistry], Georg-Thieme-Verlag, Stuttgart). However, it is also possible to use other processes which are known from the literature, but are not explained in greater detail here, for the preparation of compounds of the formula II.

The term methanesulfinate denotes an alkali metal salt of methanesulfinic acid, in particular sodium methanesulfinate or potassium methanesulfinate, or an alkaline earth metal salt of methanesulfinic acid, in particular calcium methanesulfinate or magnesium methanesulfinate. Particular preference is given to the use of sodium methanesulfinate.

The reaction of the compound of the formula II with a methanesulfinate, preferably sodium methanesulfinate, is carried out analogously to the method of A. Ulman et al., J. Org. Chem. 1989, 54, 4691–4692. The reaction is preferably carried out in a polar solvent and at reaction temperatures between 10 and 200°, preferably between 50 and 180°, particularly preferably between 80 and 140°. Particularly preferred solvents are dimethyl sulfoxide (DMSO), N,N-dimethylformamide (DMF) or 1-methyl-2-pyrrolidone (NMP), very particularly preferably DMF or NMP. The methanesulfinate is generally employed in excess. Under the said reaction conditions, exclusively the 4,5-bismethanesulfonyl-2-methylbenzoic acid of the formula III is formed.

The guanidination of the compound of the formula III in step 2 is not restricted to the acid chloride method, in which, for example, the compound of the formula III is reacted with thionyl chloride to give the acid chloride and further with guanidine. There is a large number of methods known from the literature which enable the introduction of a guanidino group (for example in the standard works, such as Houben-Weyl, Methoden der organischen Chemie [Methods of Organic Chemistry], Georg-Thieme-Verlag, Stuttgart).

For a guanidination in step 2, it is possible, inter alia, to react the free acid of the formula III with N-(benzyloxycarbonyl)guanidine, with the subsequent removal of the benzyloxycarbonyl protecting group (abbreviation=Z) liberating the guanidino group, as described in DE 199 19 349. For the preparation of benzyloxycarbonylguanidine, see M. Goodman et al., PCT Int. Appl. WO 9852917, 1998, K. Nowak, Rocz. Chem. 1969, 43, 231–232 or R. Krug and K. Nowak, Rocz. Chem. 1967, 41, 1087–1091). The coupling is carried out with the aid of the known Mukaiyama method, cf. T. Mukaiyama, Angew. Chem., Int. Ed. Engl. 1979, 18, 707–721. The removal of the Z protecting group by catalytic hydrogenation can be carried out under the general conditions for this purpose (lit.: T. W. Greene, P. G. M. Wuts, *Protective Groups in Organic Chemistry*, 2nd Edn., Wiley, New York 1991 or P. J. Kocienski, *Protecting Groups*, 1st Edn., Georg Thieme Verlag, Stuttgart—New York, 1994)

The base N-(4,5-bismethanesulfonyl-2-methylbenzoyl) guanidine prepared in accordance with the invention in steps 1 and 2 can also be converted into a salt by methods known from the literature by means of acids other than HCl. The acids which are suitable for this purpose are disclosed in EP 0 785 644.

In the method described in EP 0 758 644 for the preparation of sulfonylbenzoylguanidines, the sulfonyl group in the para-position to the carboxyl group is introduced via a nucleophilic halogen-sulfur alkyl exchange in addition to subsequent oxidation of the resultant thiophenol ether.

The process now present in this invention introduces the sulfonyl group in he para-position in a single-stage reaction step. The number of synthesis steps and the preparation costs associated therewith are reduced. Furthermore, the reaction with methyl mercaptam and the oxidation, which make particular technical safety measures necessary on a large industrial scale due to the possibility of peracid formation, are absent.

An effective process is thus available for the preparation of N-(4, 5-bismethanesulfonyl-2-methylbenzoyl)guanidine, hydrochloride and its hydrochloride hydrate which is significantly improved compared with the process known hitherto, both with respect to the number of synthesis steps and also with respect to the overall yield.

Even without further comments, it is assumed that a person skilled in the art will be able to utilise the above description in the broadest scope. The preferred embodiments should therefore merely be regarded as descriptive disclosure which is absolutely not limiting in any way.

The complete disclosure content of all applications and publications mentioned above and below are incorporated into this application by way of reference.

All temperature data above and below are given in ° C.

EXAMPLE

1. Synthesis of 4,5-Bismethanesulfonyl-2-methylbenzoic Acid 6 kg of 4-chloro-2-methyl-5-(methylsulfonyl)benzoic acid are dissolved in 15 l of N,N-dimethylformamide (DMF) at room temperature (25°) and subsequently warmed to 50°. 3.6 kg of sodium methanesulfinate are added to this solution. The internal temperature is then raised to 120° and stirred at this temperature for 2 days, with a further 3 kg of sodium methanesulfinate being added after 24 hours. After cooling to 25°, the reaction mixture is introduced into 40 l of water, and 300 g of activated carbon and 1 kg of kieselguhr are added. 5 l of ice are added to the filtrate, and 3.5 l of concentrated hydrochloric acid are added dropwise (pH=1). Recrystallisation from 2-propanol gives 3.8 kg of 4,5-bismethanesulfonyl-2-methylbenzoic acid; m.p. 234–235°.

2. Synthesis of N-(4,-Bismethanesulfonyl-2-methylbenzoyl)guanidine 2.1 Synthesis of the Acid Chloride 15 l of thionyl chloride are initially introduced at 40°, and 50 ml of DMF are added. 3.8 kg of 4,5-bismethanesulfonyl-2-methylbenzoic acid are slowly introduced with stirring, and the mixture is then stirred at the boiling point for 1 hour. After cooling, the excess SOCl₂ is removed, and the residue is codistilled a number of times with 5 l of toluene, giving 4,5-bismethanesulfonyl-2-methylbenzoyl chloride, which is reacted further as the crude product.

2.2. Synthesis of the Guanidine 1.4 kg of sodium are dissolved in 15 l of boiling methanol under a protective gas and diluted with a further 10 l of methanol. 5.9 kg of guanidinium hydrochloride are added to the solution, cooled to 20–22°, and the mixture is stirred for 1 hour. The resultant sodium chloride is then filtered off, and the solution is evaporated. The residue is codistilled with toluene and then taken up in 10 l of DMF.

2.3 Synthesis of N-(4,5-Bismethanesulfonyl-2-methylbenzoyl)guanidine

A solution of 4,5-bismethanesulfonyl-2-methylbenzoyl chloride, prepared as described in 2.1., in 5 l of DMF is added dropwise at 12° to the guanidine solution prepared as described in 2.2. The reaction mixture is stirred at 20° for 5 hours, and 45 l of cold water (0–50) are added slowly. The deposited crystals are filtered off and rinsed with ice-water, acetonitrile and diethyl ether. The crude crystals are dissolved in 315 l of hot acetonitrile/water (20:1). The solution is treated with 200 g of activated carbon, filtered and cooled to 0°, giving N-(4,5-bismethanesulfonyl-2-methylbenzoyl) guanidine as the acetonitrile adduct in a yield of 64.8%; m.p. 233–2340 °.

3.1. Synthesis of N-(4,5-Bismethanesulfonyl-2-methylbenzoyl)guanidine, Hydrochloride Hydrate 2.7 kg of N-(4,5-bismethanesulfonyl-2-methylbenzoyl) guanidine are suspended in 25 l of water at 60°, and 10.6 l of 1N HCl solution are added. On warming to 80°, a clear solution is obtained. The solution is allowed to cool slowly, with crystallisation beginning at 50°, giving N-(4, 5-bismethanesulfonyl-2-methylbenzoyl)guanidine, hydrochloride hydrate in a yield of 97%, m.p. 181–188 °.

3.2. Synthesis of N-(4,-Bismethanesulfonyl-2-methylbenzoyl)guanidine, Hydrochloride The N-(4,5-bismethanesulfonyl-2-methylbenzoyl) guanidine, hydrochloride hydrate obtained from 3.1. is dried to constant weight at 120° under reduced pressure, giving N-(4,5-bismethanesulfonyl-2-methylbenzoyl)guanidine, hydrochloride.

3.3. Synthesis of N-(4,5-Bismethanesulfonyl-2-methylbenzoyl)guanidine, Hydrochloride 2.7 kg of N-(4,5-bismethanesulfonyl-2-methylbenzoyl) guanidine are suspended in 25 l of ethanol at 60°, and 10.6 l of 1N HCl solution are added. On warming to 80°, a clear solution is obtained. The solution is allowed to cool slowly, with crystallisation beginning at 50°, The N-(4, 5-bismethanesulfonyl-2-methylbenzoyl)guanidine, hydrochloride obtained is subsequently dried to constant weight at 60°, giving N-(4,5-bismethanesulfonyl-2-methylbenzoyl) guanidine, hydrochloride.

What is claimed is:

1. N-(4,5-Bismethanesulfonyl-2-methylbenzoyl) guanidine, hydrochloride hydrate.

2. A process for the preparation of N-(4,5-bismethanesulfonyl-2-methylbenzoyl)guanidine, hydrochloride of the formula I,

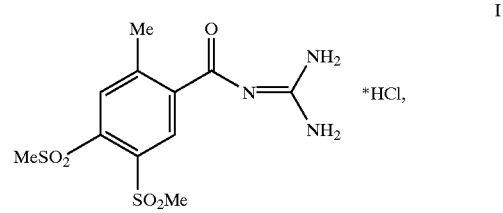

in which Me is methyl, and of the hydrochloride hydrate, which is characterised in that firstly, by reaction of the starting compound of the formula II

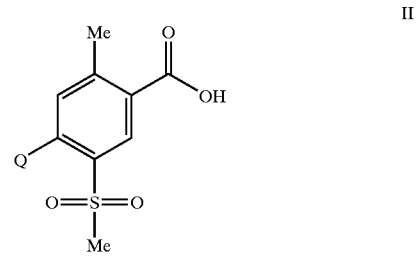

in which

Me is a methyl group, and Q is fluorine or chlorine, with a methanesulfinate in a nucleophilic substitution, the 4-methanesulfonyl group is introduced in a one-step reaction, then, in the second step, the compound of the formula III

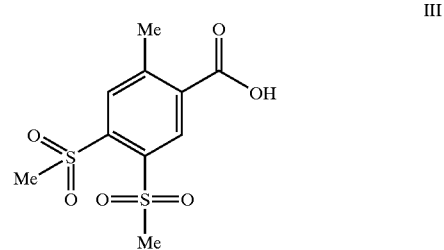

is converted into the acid chloride and reacted with guanidine to give N-(4,5-bismethanesulfonyl-2-methylbenzoyl) guanidine, and, in the third step, converted into the hydrochloride of the formula I and/or the hydrochloride hydrate by reaction in aqueous HCl.

3. A process according to claim 2, characterised in that sodium methanesulfinate is used in the first step.

4. A process according to claim 2, characterized in that a polar solvent is used in the first step.

5. A process according to claim 2, characterised in that a reaction temperature of between 80 and 140° is set in the first step.

* * * * *

UNITED STATES PATENT AND TRADEMARK OFFICE
CERTIFICATE OF CORRECTION

PATENT NO. : 6,673,968 B1
DATED : January 6, 2004
INVENTOR(S) : Rolf Gericke et al.

It is certified that error appears in the above-identified patent and that said Letters Patent is hereby corrected as shown below:

Column 6,
Line 19, reads "which is characterised in that," should read -- which comprises: --
Line 20, reads "firstly, by reaction of the," should read -- reacting in a first step --
Line 37, reads "methanesulfonyl," should read -- methane-sulfonyl --
Line 37, reads "group is introduced," should read -- group being introduced --
Line 39, reads "the second step, the" should read -- a second step, coverting --
Line 52, should delete "is converted"
Line 52, reads "reacted," should read -- reacting --
Line 55, reads "in the third step, converted," should read -- in a third step, converting --
Line 58, reads "characterised," should read -- characterized --
Line 59, reads "methanesulfinate," should read -- methane-sulfinate --
Line 63, reads "characterized in that, should read -- wherein --
Line 64, reads "140 " should read -- 140°C is --
Line 66, insert the following claims:
-- 6. The process of claim 2, wherein the reaction in the first step is carried out at a reaction temperature between 10 and 200°C.
   7. The process of claim 2, wherein the reaction in the first step is carried out at a reaction temperature between 50 and 180°C.
   8. The process of claim of claim 4, wherein the polar solvent is DMSO, DMF or NMP.
   9. The process of claim 2, wherein, in the second step, the compound of formula III is converted to the acid chloride by reacting with thionyl chloride. --

Signed and Sealed this

Seventeenth Day of August, 2004

JON W. DUDAS
*Acting Director of the United States Patent and Trademark Office*